United States Patent
Sumaily

(10) Patent No.: US 10,856,841 B1
(45) Date of Patent: Dec. 8, 2020

(54) ULTRASONIC IMAGING PROBE

(71) Applicant: KING SAUD UNIVERSITY, Riyadh (SA)

(72) Inventor: Ibrahim Ali Sumaily, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/752,584

(22) Filed: Jan. 24, 2020

(51) Int. Cl.
*A61B 8/00* (2006.01)
*A61B 1/233* (2006.01)
*A61B 1/015* (2006.01)
*A61B 8/12* (2006.01)

(52) U.S. Cl.
CPC ............ *A61B 8/4281* (2013.01); *A61B 8/445* (2013.01); *A61B 8/461* (2013.01); *A61B 1/015* (2013.01); *A61B 1/233* (2013.01); *A61B 8/12* (2013.01)

(58) Field of Classification Search
CPC ....... A61B 8/4281; A61B 8/461; A61B 8/445; A61B 8/12; A61B 1/233; A61B 1/015
See application file for complete search history.

(56) References Cited

U.S. PATENT DOCUMENTS

| 5,634,466 A | 6/1997 | Gruner | |
| 6,572,547 B2* | 6/2003 | Miller | A61B 5/6819 600/437 |
| 7,844,320 B2* | 11/2010 | Shahidi | A61B 5/064 600/424 |
| 10,258,225 B2* | 4/2019 | Bendory | A61B 1/233 |
| 2007/0093712 A1 | 4/2007 | Byron | |
| 2008/0119738 A1* | 5/2008 | Imahashi | A61B 1/0055 600/462 |
| 2009/0005688 A1* | 1/2009 | Wakabayashi | A61B 8/445 600/462 |

(Continued)

FOREIGN PATENT DOCUMENTS

JP  2005312838 A  11/2005

OTHER PUBLICATIONS

Long-Jun He et al., "Ultrasound-guided fine needle aspiration of retropharyngeal lymph nodes after radiotherapy for nasopharyngeal carcinoma: a novel technique for accurate diagnosis", Cancer Communications (2018), 38:20, 8 pages.

(Continued)

*Primary Examiner* — Sanjay Cattungal
(74) *Attorney, Agent, or Firm* — Nath, Goldberg & Meyer; Richard C. Litman

(57) ABSTRACT

The ultrasonic imaging probe includes a proximal handle, a shaft extending distally from the handle, and an ultrasonic transducer attached to the distal end of the shaft. The shaft may define multiple bends to assist in properly positioning the transducer when the probe is inserted through the sinus of a patient. An ultrasound communications fiber extends through the probe to the transducer. A tube that may be used for dispensing an ultrasound gel extends out from the handle and follows the length of the shaft for dispensing ultrasound gel on the transducer and surrounding tissue. The ultrasonic transducer transmits ultrasonic waves and detects reflected ultrasonic waves for creating an image of structures within the tissue. A data cable extending proximally out from the handle is adapted to transmit the data from the reflected waves to a monitor, which produces a real-time image from the data.

6 Claims, 3 Drawing Sheets

(56) References Cited

U.S. PATENT DOCUMENTS

| | | | |
|---|---|---|---|
| 2009/0118621 A1* | 5/2009 | Harhen | A61B 1/0051 600/466 |
| 2011/0060185 A1* | 3/2011 | Ikuma | A61B 5/7214 600/104 |
| 2011/0125026 A1* | 5/2011 | Neto | A61B 8/06 600/463 |
| 2011/0263983 A1* | 10/2011 | Peszynski | A61B 1/0052 600/443 |
| 2013/0281844 A1* | 10/2013 | Karino | A61B 8/12 600/427 |
| 2014/0012276 A1* | 1/2014 | Alvarez | A61B 17/2202 606/107 |
| 2015/0133779 A1* | 5/2015 | Yurek | A61B 8/12 600/435 |
| 2016/0310042 A1 | 10/2016 | Kesten et al. | |
| 2018/0132927 A1 | 5/2018 | Chen et al. | |
| 2019/0117193 A1* | 4/2019 | Cuscuna | A61M 25/0138 |

OTHER PUBLICATIONS

Sastry et al., "Applications of Ultrasound in the Resection of Brain Tumors", J. Neuroimaging (2017), 27(1), pp. 5-15.

* cited by examiner

ULTRASONIC IMAGING PROBE

BACKGROUND

1. Field

The present disclosure relates to surgical implements for endoscopic surgery, and particularly to an ultrasonic imaging probe for intraoperative ultrasonic imaging for navigation during endoscopic sinus surgery or endoscopic surgery on the brain or cranium.

2. Description of the Related Art

Endoscopic sinus surgery is one of the most common surgeries conducted for paranasal sinus disease, as well as for operation on the skull base and operations to treat intracranial diseases. Many operations in the paranasal region and on the skull base are performed near vital structures where errors of 1 mm may cause serious injuries.

Over the last three decades, the computed tomography (CT) navigation and magnetic resonance imaging (MRI) navigation guided surgery has increased safety and accuracy of the above mentioned procedures. However, CT navigation uses preoperative CT images to guide the surgeon. In many cases, preoperative CT images do not provide images that remain accurate throughout a surgical procedure, since anatomical structures may be changed by the actions of the surgeon. As a result, the surgeon is required to predict where anatomical features have shifted from the preoperative CT image while performing a procedure, which may result in errors. MRI navigation suffers from similar preoperative imaging problems.

Thus, an ultrasonic imaging probe solving the aforementioned problems is desired.

SUMMARY

The ultrasonic imaging probe includes a proximal handle, a shaft extending distally from the handle, and an ultrasonic transducer attached to the distal end of the shaft. The shaft may define multiple bends to assist in properly positioning the transducer when the probe is inserted through the sinus of a patient. An ultrasound communications fiber extends through the probe to the transducer. A tube that may be used for dispensing an ultrasound gel extends out from the handle and follows the length of the shaft for dispensing ultrasound gel on the transducer and surrounding tissue. The ultrasonic transducer transmits ultrasonic waves and detects reflected ultrasonic waves for creating an image of structures within the tissue. A data cable extending proximally out from the handle is adapted to transmit the data from the reflected waves to a monitor, which produces a real-time image from the data.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The ultrasonic imaging probe includes a proximal handle, a shaft extending distally from the handle, and an ultrasonic transducer attached to the distal end of the shaft. The shaft may define multiple bends to assist in properly positioning the transducer when the probe is inserted through the sinus of a patient. An ultrasound communications fiber extends through the probe to the transducer. A tube that may be used for dispensing an ultrasound gel extends out from the handle and follows the length of the shaft for dispensing ultrasound gel on the transducer and surrounding tissue. The ultrasonic transducer transmits ultrasonic waves and detects reflected ultrasonic waves for creating an image of structures within the tissue. A data cable extending proximally out from the handle is adapted to transmit the data from the reflected waves to a monitor, which produces a real-time image from the data.

Figure 1:
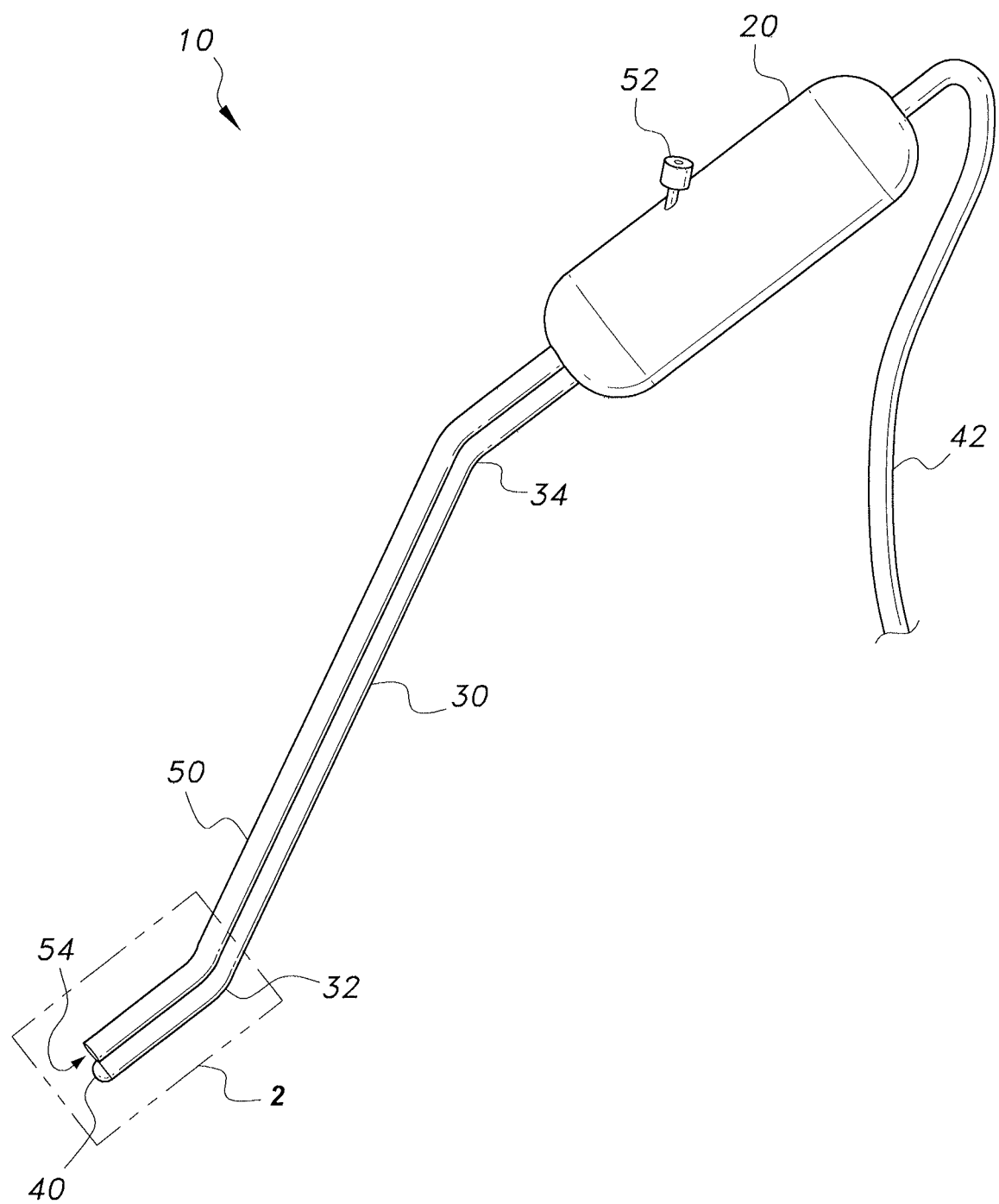
FIG. 1 is a perspective view of an ultrasonic imaging probe.

FIG. 1 shows an embodiment of the ultrasonic imaging probe 10 including a distal ultrasonic transducer 40 attached to a proximal handle 20 by a shaft 30. The ultrasonic transducer 40 may be any ultrasonic transducer known in the art for medical imaging having a diameter less than 0.75 cm or having a diameter capable of being inserted through a nostril. The shaft 30 may define a proximal bend 34, which is angled downwards, and a distal bend 32, which is angled upwards, opposite the proximal bend 34. The distal bend 32 angles the transducer 40 for contact with the skull base when the probe 10 is inserted through a patient's sinus. The proximal bend 32 places the handle 20 in a position more easily operated by the practitioner by aligning the handle 20 with the distal tip of the shaft 30. A power and data cord 42 or ultrasound imaging communications cable (such as micro coaxial cable) may extend through the shaft 30 between the handle 20 and the ultrasonic transducer 40. The cord 42 may also extend proximally out of the handle 20 for attachment to a computer, ultrasound imaging monitor, or similar device for displaying the ultrasonic image. The handle 20 may be designed to be easily gripped and manipulated by a practitioner. For example, as shown in FIG. 1, the handle 20 may be cylindrically shaped.

An ultrasonic gel injection tube 50 may extend along a length of the shaft 30 from the handle 20 to the distal end of the shaft 30. The ultrasonic gel tube 50 may be fed through a gel injection port 52 located on the handle 20. Ultrasonic gel (for reducing the adverse effect of air bubble on the transmission of ultrasound) may be dispensed on the ultrasonic transducer 40, and on tissue to be contacted by the ultrasonic transducer 40, by the ultrasound gel tube 50. A tip of a syringe 70 (shown in FIG. 3) filled with ultrasound gel may be inserted into the gel injection port 52 and ultrasound gel may be forced through the ultrasound gel tube 50 by dispensing the ultrasound gel from the syringe 70. An assisting surgeon or scrub nurse may assist a primary surgeon operating the probe 10 by operating the ultrasonic gel syringe 70. The tube 50 may also be used for applying suction adjacent the transducer 40 to clear the area around the transducer 40.

Figure 2:
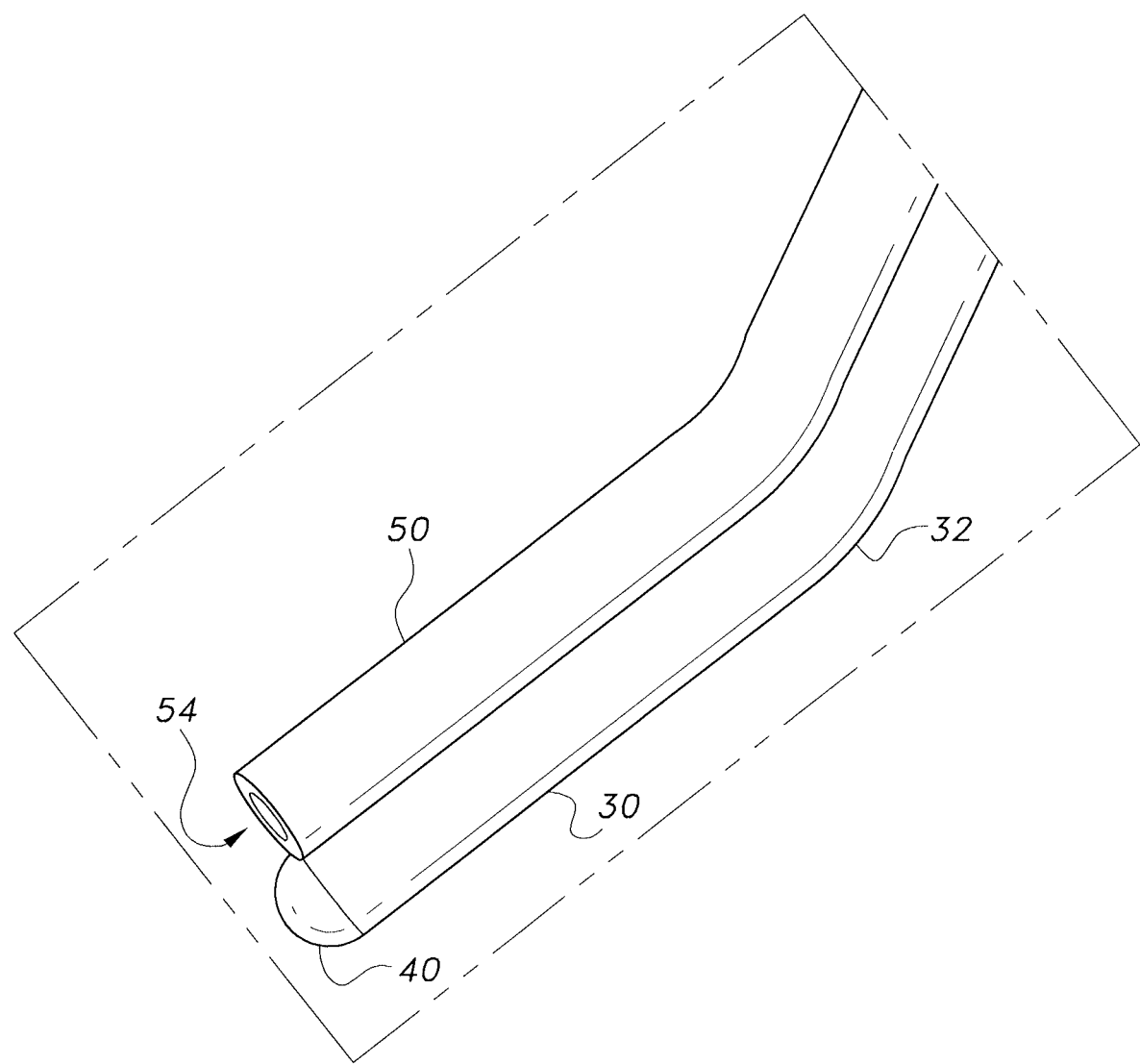
FIG. 2 is a detail perspective view area 2 of FIG. 1, showing the tip for dispensing ultrasonic gel adjacent the ultrasonic transducer.

FIG. 2 shows a detail view of the distal tip of the ultrasonic imaging probe 10. The ultrasonic transducer 40 is attached to the distal end of the shaft 30. A distal outlet 54 of the ultrasonic gel tube 50 is positioned immediately above the ultrasonic transducer 40. The proximity of the distal outlet 54 of the ultrasonic gel tube 50 and the ultrasonic transducer 40 results in the ultrasound gel being dispensed directly on the ultrasonic transducer 40 and the tissue being contacted by the ultrasonic transducer 40 to ensure there is a proper conductive interface between the ultrasonic transducer 40 and the tissue being imaged.

The proximal bend 34 and distal bend 32 of the shaft 30 may have equal angular variance in opposite directions resulting in the handle 20 and distal tip of the shaft 30 extending in parallel. The distal bend 32 and portion of the shaft 30 distal to the distal bend 32 may be made from a more flexible material than the proximal shaft 30 portions and/or may include a hinging mechanism that provides additional flexibility. The distal tip of the shaft 30 may be designed to provide 45° of flexion to accommodate use in multiple locations of the sinus from the frontal sinus to the clivus. Exemplary dimensions may include, for example, a distance between the distal tip of the shaft 30 and the distal bend 32 of approximately 1.5 cm; a distance between the distal bend 32 and the proximal bend 34 of approximately 12 cm; a distance between the proximal bend 34 and the handle 20 of approximately 2 cm; and a length of the handle 20 of approximately 5 cm. The proximal bend 34 and distal bend 32 may provide an angle in the range of 15° to 45°.

Figure 3:
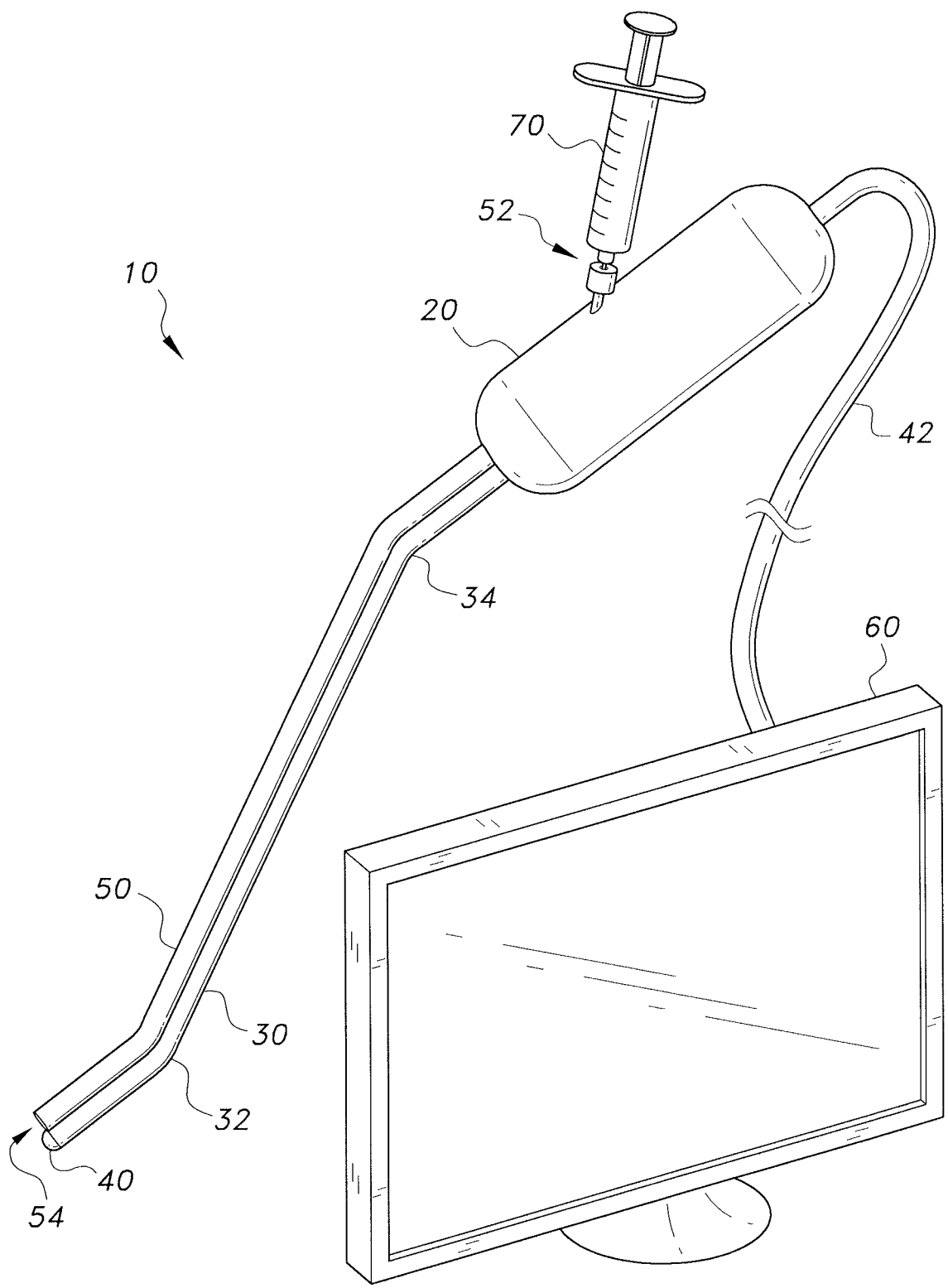
FIG. 3 is a perspective view of an exemplary imaging system incorporating the ultrasonic imaging probe of FIG. 1.

FIG. 3 shows an ultrasonic imaging system for endoscopic procedures that includes the ultrasonic imaging probe 10. The proximally extending cord 42 of the imaging probe 10 may terminate at a data and power connector, such as a USB adapter. The cord 42 may be connected to a port of a computer 60 or monitor for processing the data received by the ultrasonic transducer 40 and displaying a real-time image of the tissue being imaged by the ultrasonic transducer 40. In addition, power may be provided to the ultrasonic transducer 40 through the computer's port. The computer 60 may be any computing device known in the art having a processor, memory, and a display, such as a personal desktop computer, laptop computer, or handheld computing device. In some embodiments, the ultrasonic transducer 40 may be powered by a battery located in or on the probe and may communicate with the computer via a wireless connection.

The ultrasonic imaging probe 10 may be used during a surgical procedure when the surgeon requires real-time image-guided navigation. The multi-bend shaft 30 of the probe allows the surgeon to visualize anatomical structures, such as the skull base, ethmoid arteries, orbit, optic nerve, and carotid artery for performing surgery around these structures without damaging surrounding tissue intended to be left unharmed. Real-time ultrasonic imaging is especially usefully when surgical landmarks are disrupted and computerized tomography or magnetic resonance imaging navigation, based on pre-procedure imaging, cannot be reliably used.

It is to be understood that the ultrasonic imaging probe is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. An ultrasonic imaging probe, comprising:
    a handle adapted for gripping by a user;
    a shaft having a proximal end and a distal end, the proximal end extending from the handle, the shaft defining a downward proximal bend proximal to the handle and an upward distal bend distal from the handle, wherein each of the bends provide an angle in the range of 15° to 45°;
    an ultrasonic transducer attached to the distal end of the shaft; wherein the distal end of the shaft is more flexible than the remainder of the shaft;
    a ultrasound gel tube extending along a length of the shaft, the ultrasound gel tube defining a lumen extending therethrough, the lumen having a distal end adjacent the ultrasonic transducer;
    a port extending from the handle, the port being in fluid communication with the lumen defined by the ultrasound gel tube; wherein the ultrasonic transducer and the shaft are dimensioned and configured for insertion into a patient's paranasal cavity through the patient's nostril; and
    an ultrasound communication cable for medical imaging extending from the ultrasonic transducer through the shaft and out a proximal end of the handle, the cable being adapted for attachment to a device for displaying ultrasound images.

2. The ultrasonic imaging probe of claim 1, wherein a portion of the shaft proximal to the proximal bend is parallel to a portion of the shaft distal from the distal bend.

3. The ultrasonic imaging probe of claim 1, wherein the port is adapted for receiving an ultrasonic gel injected from a syringe.

4. The ultrasonic imaging probe of claim 1, wherein the shaft and the ultrasonic gel tube are connected along their lengths.

5. The ultrasonic imaging probe of claim 1, wherein the ultrasonic transducer is configured for ultrasonic imaging.

6. The ultrasonic imaging probe of claim 1, wherein the proximal bend and the distal bend have equal angular variance.

* * * * *